United States Patent [19]

Vyas et al.

[11] Patent Number: 4,691,023

[45] Date of Patent: Sep. 1, 1987

[54] AMINO DISULFIDES

[75] Inventors: Dolatrai M. Vyas, Fayetteville, N.Y.; Yulin Chiang, Morristown, N.J.; Terrence W. Doyle, Fayetteville, N.Y.

[73] Assignee: Bristol-Myers Company, New York, N.Y.

[21] Appl. No.: 894,602

[22] Filed: Aug. 7, 1986

Related U.S. Application Data

[60] Division of Ser. No. 581,291, Feb. 24, 1984, which is a continuation-in-part of Ser. No. 484,016, Apr. 11, 1983, abandoned.

[51] Int. Cl.$^4$ .................... C07D 487/14; H61K 31/40
[52] U.S. Cl. ...................... 548/422; 548/136; 548/159; 548/181; 548/221; 548/251; 548/265; 548/327; 548/336; 546/157; 546/199; 546/271; 544/142; 544/316; 544/372; 540/602
[58] Field of Search .......................... 548/422

[56] References Cited

U.S. PATENT DOCUMENTS

| | | | |
|---|---|---|---|
| 3,332,944 | 7/1967 | Cosulich et al. | 548/422 |
| 3,420,846 | 1/1969 | Matsui et al. | 548/422 |
| 3,450,705 | 6/1969 | Matsui et al. | 548/422 |
| 3,514,452 | 5/1970 | Matsui et al. | 548/422 |
| 3,660,578 | 5/1972 | Hata et al. | 548/422 |
| 4,231,936 | 11/1980 | Nakano et al. | 548/422 |
| 4,268,676 | 5/1981 | Remers | 548/422 |

FOREIGN PATENT DOCUMENTS 892162   5/1982  Belgium .

OTHER PUBLICATIONS

J. Amer. Chem. Soc. 84, 3185-3187 (1962), J. S. Webb et al.
The Journal of Antibiotics, XXI, 189-198 (1968), Matsui et al.
J. Med. Chem. 14, 103-109 (1971), Kinoshita et al.
J. Med. Chem. 24, 975-981 (1981), Iyengar et al.
Physicians' Desk Reference, 35th Edition, 1981, pp. 717-718.
Iyengar et al.—Abstracts of Papers, 183rd Annual Meeting of the American Chemical Society, Mar. 1982, No. MEDI 72.
C. A. Claridge et al.—Abst. of the Annual Meeting of Amer. Soc. for Microbiology, 1982, Abs. 028.
J. Med. Chem., 1983, 26, 16-20, Iyengar et al.
Iyengar et al., Abstracts of Papers, 185th Annual Meeting of the American Chemical Society, Mar. 1983, No. MEDI 82.
Farmdoc No. 56227 D/31.
American Association of Cancer Research Poster Material presented May 25, 1983 in San Diego, California.
Shirahata et al., J. Am. Chem. Soc., 1983, 105, 7199-7200.

Primary Examiner—Donald G. Daus
Assistant Examiner—William A. Teoli, Jr.
Attorney, Agent, or Firm—Robert E. Carnahan

[57] ABSTRACT

The present invention refers to mitomycin analogs containing a disulfide group. These compounds are mitomycin C derivatives in which the 7-amino group bears an organic substituent incorporating a disulfide group. The compounds are inhibitors of experimental animal tumors.

1 Claim, No Drawings

AMINO DISULFIDES

REFERENCE TO RELATED APPLICATION

This application is a division of co-pending application Ser. No. 581,291 filed Feb. 24, 1984 which is a continuation-in-part of Ser. No. 484,016 filed Apr. 11, 1983 and now abandoned.

FIELD OF THE INVENTION

The present invention refers to mitomycin analogs containing a disulfide group (Class 260 Subclass 326.24). These compounds are mitomycin C derivatives in which the 7-amino group bears an organic substituent incorporating a disulfide group. These compounds are inhibitors of experimental animal tumors.

Nomenclature—The systematic Chemical Abstracts name for mitomycin C is:
[1aR-(1aα,8β,8aα,8bα)]-6-amino-8-[((aminocarbonyl)oxy)methyl]-1,1a,2,8,8a,8b-hexahydro-8a-methoxy-5-methyl-arizino[2′,3′,3,4,]pyrrolo[1,2-a] indole-4,7-dione
according to which the azirinopyrroloindole ring system is numbered as follows:

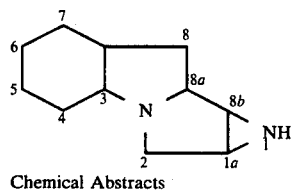

Chemical Abstracts

A trivial system of nomenclature which has found wide use in the mitomycin literature identifies the foregoing ring system including several of the characteristic substituents of the mitomycins as mitosane.

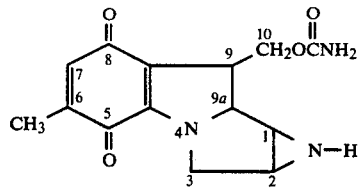

Mitosane

We have chosen in the present specification to use this system and to refer to the azirino nitrogen atom as $N^{1a}$ and the ring amino nitrogen atom as $N^7$. As to the stereochemical configuration of the products of this invention, it is intended when identifying them by the root name "mitosane" or by structural formula to identify the stereochemical configuration thereof as the same as that of mitomycin C.

DESCRIPTION OF THE PRIOR ART

Mitomycin C is an antibiotic which is produced by fermentation and is presently on sale under Food and Drug Administration approval for the therapy of disseminated adenocarcinoma of the stomach or pancreas in proven combinations with other approved chemotherapeutic agents and as palliative treatment when other modalities have failed (Mutamycin ® Bristol Laboratories, Syracuse, N.Y. 13201, Physicians' Desk Reference 35th Edition, 1981, pp. 717 and 718). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al. of Lederle Laboratories Division American Cyanamid Company, J. Amer. Chem. Soc. 84, 3185–3187 (1962). One of the chemical transformations used in this structure study to relate mitomycin A and mitomycin C was the conversion of the former, 7-9α-dimethoxymitosane, by reaction with ammonia to the latter, 7amino-9α-methoxymitosane. Displacement of the 7-methoxy group of mitomycin A has proven to be a reaction of considerable interest in the preparation of antitumor active derivatives of mitomycin C. The following articles and patents each deal with the conversion of mitomycin A to a 7-substituted amino mitomycin C derivative having antitumor activity. The object of this research was to prepare derivatives which were more active, and particularly which were less toxic than mitomycin C:

Matsui et al. "The Journal of Antibiotics", XXI, 189–198 (1968).
Kinoshita et al. J. Med. Chem. 14 103–109 (1971).
Iyengar et al. J. Med. Chem. 24, 975–981 (1981).
Iyengar, Sami, Remers, and Bradner, Abstracts of Papers 183rd Annual Meeting of the American Chemical Society, March 1982, No. MEDI 72.
Iyengar, et al. J. Med. Chem. 1983, 26, 16–20.
Iyengar, et al. Abstracts of Papers, 185th
Annual Meeting of the American Chemical Society, March 1983, No. MEDI 82.

The following patents deal with the preparation of 7-subtituted aminomitosane derivatives by the reaction of mitomycin A, mitomycin B, or an $N^{1a}$-substituted derivative thereof with a primary or secondary amine:

Cosulich et al. U.S. Pat. No. 3,332,944 patented July 25, 1967.
Matsui et al. U.S. Pat. No. 3,420,846 patented Jan. 7, 1969.
Matsui et al. U.S. Pat. No. 3,450,705 patented June 17, 1969.
Matsui et al. U.S. Pat. No. 3,514,452 patented May 26, 1970.
Nakano et al. U.S. Pat. No. 4,231,936 patented Nov. 4, 1980.
Remers, U.S. Pat. No. 4,268,676 patented May 19, 1981.
Remers, Belg. No. 893,162, patented May 12, 1982.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al. Abst. of the Annual Meeting of Amer. Soc. for Microbiology 1982. Abs. 028).

Mitomycin C is the principal mitomycin produced by fermentation and is the commercially available form. Current technology for the conversion of mitomycin C to mitomycin A for use in the production of the semisynthetic substituted amino analogs of mitomycin C referred to in the foregoing patents and publications involves hydrolysis of mitomycin C to the corresponding 7-hydroxymitosane, a highly unstable compound, and then methylation of that substance with diazomethane which is a very hazardous substance to handle. One attempt to avoid the use of diazomethane for methylation involves the use of 7-acyloxymitosanes (Kyowa Hakko Kogyo KK Japanese Pat. No. J5 6073-085, Farmdoc No. 56227 D/31) for mitomycin C analog synthesis.

SUMMARY OF THE INVENTION

The present invention is concerned with a group of mitomycin C analogs having a dithio organic substituent on the amino nitrogen atom in the 7-position. These compounds may be represented by the following formula

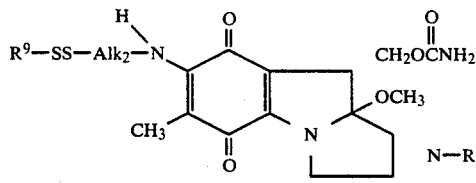

wherein $R^9$ is an organic group, viz. the structural component of an organic thiol of the formula $R^9SH$, and $Alk_2$ and R have the meanings given below. These compounds are alternatively described by Formulas I and II

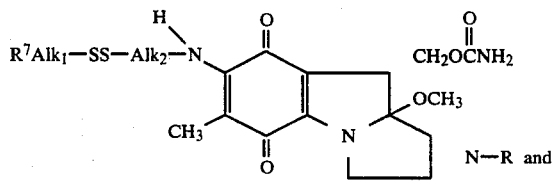

I

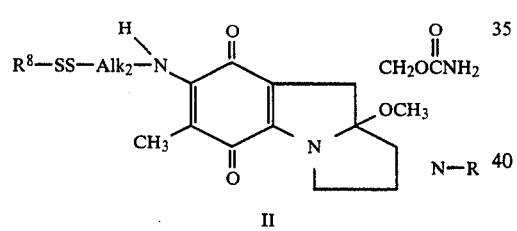

II wherein:

$Alk_1$ is a straight or branched chain alkylene group having 1 to 6 carbon atoms when $R^7$ is joined thereto through a carbon atom thereof, and 2 to 6 carbon atoms when $R^7$ is joined thereto through a sulfur, oxygen, or nitrogen atom thereof, and $R^7$ and —SS— are in that instance joined to different carbon atoms $Alk_2$ is a straight or branched chain alkylene group having 2 to 6 carbon atoms optionally bearing an $R^7$ substituent wherein the sulfur and nitrogen atoms connected thereto and any optional $R^7$ substituent connected thereto through oxygen sulfur or nitrogen are attached to different carbon atoms of $Alk_2$, $Alk_1$ and $Alk_2$ may contain a double bond, R is hydrogen, lower alkyl, lower alkanoyl, benzoyl, or substituted benzoyl wherein said substituent is lower alkyl, lower alkoxy, halo, amino, or nitro, $R^7$ is selected from the group consisting of hydroxy, halo, amino, alkylamino or dialkyamino having 1 to 12 atoms, alkanoylamino, benzoylamino or A-substituted benzoylamino, naphthoylamino or A-substituted naphthoylamino, cycloalkyl or A-substituted cycloalkyl each having 3 to 8 ring members, cycloalkenyl or A-substituted cycloalkenyl each having 5 to 8 ring members, phenyl or A-substituted phenyl, naphthyl or A-substituted naphthyl, a heterocyclic group selected from the group consisting of heteroaromatic and heteroalicyclic groups having from 1 to 2 rings, from 3 to 8 ring members in each ring, and from 1 to 4 hetero atoms selected from oxygen, nitrogen, and sulfur, alkoxy or alkylthio each having 1 to 6 carbon atoms, carboxy, alkoxycarbonyl having 1 to 7 carbon atoms, phenoxycarbonyl or A-substituted phenoxycarbonyl, phenoxy or A-substituted phenoxy, naphthoxy or A-substituted naphthoxy, alkoxycarbonylamino having 2 to 6 carbon atoms, guanidino, ureido (—NHCONH$_2$), N-alkylureylene (—NHCONHalkyl) having 2 to 7 carbon atoms, $N^3$-haloalkylureylene having 3 to 7 carbon atoms, $N^3$-haloalkyl-$N^3$-nitrosoureylene having 3 to 7 carbon atoms, and dialkylaminocarbonyl having 3 to 13 carbon atoms, wherein said A substituent is selected from the group consisting of one or two lower alkyl, lower alkanoyl, lower alkoxy, halo, amino, hydroxy, or nitro groups, and $R^8$ is selected from the group consisting of alkyl having 1 to 12 carbon atoms, alkenyl or alkynyl each having 3 to 12 carbon atoms, cycloalkyl having 3 to 8 ring members, A-substituted cycloalkyl having 3 to 8 ring members, cycloalkenyl having 5 to 8 ring members, phenyl, A-substituted phenyl, naphthyl, A-substituted naphthyl, a heterocyclic group selected from the group consisting of heteroaromatic and heteroalicyclic groups having from 1 to 2 rings, from 3 to 8 ring members in each ring, and from 1 to 4 hetero atoms selected from oxygen, nitrogen, and sulfur, wherein said A substituent is selected from the group consisting of one or two lower alkyl, lower alkanoyl, lower alkoxy, halo, amino, hydroxy or nitro groups, and $R^8$ and the adjacent sulfur atom together constitute S-cysteinyl wherein said S-cysteinyl group may be esterified, salified, or joined within a peptide bond.

The substances of this invention are inhibitors of experimental tumors in animals. They are prepared by reacting an aminodisulfide of Formulas III or IV

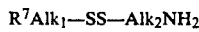

or

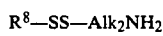

with a mitosane derivative of Formula V

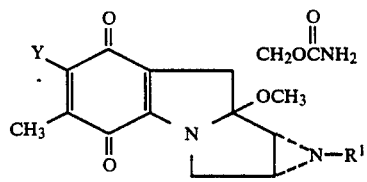

wherein Y is a group readily displacable by reaction with a primary amine to yield an $N^7$-substituted mitomycin C derivative. Such mitosane derivatives include mitomycin A and its homologs of Formula V wherein Y is a lower alkoxy group of 1 to 6 carbon atoms. Another is the derivative having Formula V wherein Y is the amidino group of Formula VI.

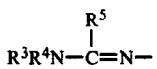

wherein:
R$^5$ is hydrogen (preferred), lower alkyl, phenyl, lower alkylphenyl, lower alkoxyphenyl, halophenyl, aminophenyl, or nitrophenyl, and R$^3$ and R$^4$ are independently lower alkyl, or together with the nitrogen atom to which they are attached constitute pyrrolidine, 2-, or 3-lower alkylpyrrolidine, piperidine, 2-, 3-, or 4-lower alkylpiperidine, 2,6-dilower alkylpiperidine, piperazine, 4-substituted piperazine (wherein said 4-substituent is alkyl, or carbalkoxy each having 1 to 8 carbon atoms, phenyl, methylphenyl, methoxyphenyl, halophenyl, nitrophenyl, or benzyl), azepine 2-, 3-, 4-, or 5-lower alkylazepine, morpholine, thiomorpholine, thiomorpholine-1-oxide, or thiomorpholine-1,1-dioxide, wherein each of the aforesaid lower alkyl, lower alkanoyl and lower alkoxy groups contains 1 to 6 carbon atoms.

The later are amidino derivatives of mitomycin c and are described in copending application Ser. No. 385,149 filed June 4, 1982.

DETAILED DESCRIPTION OF THE INVENTION

The reaction between the mitosane derivative of Formula V and the aminodisulfide of Formula III or Formula IV takes place in an anhydrous liquid organic reaction medium at a temperature in the range of from about −15° C. to +50° C. A temperature in the range of from 0° C. to 20° C. is preferred. Any anhydrous liquid organic reaction medium may be employed so long as it is stable under the reaction conditions and does not paticipate in the reaction in a deleterious way. From 1 to 4 molar portions of the aminodisulfide of Formulas III or IV are employed with the mitosane reactant of Formula V. Preferably equimolar amounts of the two reactants are employed. A reaction period of several hours and preferably from about 8 to 50 hours is employed. The product is recovered chromatographically which may suitably involve evaporating of the liquid organic reaction medium and chromatography of the residue.

Aminodisulfides of Formula III and Formula IV are known compounds and may be prepared by various methods. For instance, they may be made by reaction of the appropriate thiol R$^7$Alk$_1$SH or R$^8$SH with a Bunte salt of the formula

NH$_2$Alk$_2$SSO$_3$NA    VII or with a sulfenylthiocarbonate of the formula

                    VIII

Klayman et al. Journal of Organic Chemistry 29, 3737–3738 (1964) have prepared the following by the Bunte salt method.
2-aminoethyl n-butyl disulfide
2-aminoethyl n-hexyl disulfide
2-aminoethyl n-octyl disulfide
2-aminoethyl n-decyl disulfide
2-aminoethyl phenyl disulfide
2-aminoethyl benzyl disulfide Methanol was found to be the preferred reaction solvent for the reaction of the Bunte salt with the thiol. Reaction temperatures of 0° to −10° C. were found to be preferred using this solvent. Higher temperatures were necessary with other solvents. The chief drawback of this method is the formation of symmetrical disulfides as a by-product, presumably as a result of disproportionation of the desired mixed disulfide.

The mixed disulfide starting materials of Formulas III and Formula IV are preferably prepared via reaction of the appropriate thiol, with a sulfenylthiocarbonate of Formula VIII. This is the method of S. J. Brois et al. Journal of the American Chemical Society 92, 7269–7270 (1970). Typically this preparative procedure involves adding the thiol to a methanol solution of the amino-alkylsulfenylthiocarbonate of Formula VIII and allowing the reaction to proceed at a temperature in the range of from 0° to 25° C. Reaction times vary from virtually instantaneous to several hours depending upon the particular thiol employed. The progress of the reaction can be followed by measuring the presence of unreacted thiol in the reaction vessel. If the reaction is sluggish, a catalytic amount of trithylamine may be added as reaction accelerator.

The following is an enumeration of representative thiols of the formulas R$^7$Alk$_1$SH or R$^8$SH which may be converted via reaction with the Bunte salt VII or sulfenylthiocarbonate VIII to produce intermediates Formulas III and IV which in turn are converted to products of the present invention as described. In the case of the amino containing thiols in the following enumeration, it is generally desirable to first convert them to a protected form, preferably the β-(trimethylsilyl)ethoxycarbonylamino derivative, prior to conversion to the intermediates of Formulas III or IV and reaction with the mitosane intermediate of Formula V. The β-(trimethylsilyl)ethoxycarbonylamino group can then be subsequently cleaved by treatment with tetraethylammonium fluoride in acetonitrile (L. A. Carpino et al., J. C. S. Chem. Comm., 358 (1978)) to yield the desired free amino compound of Formula I or II.

HSCH$_3$

HSCH$_2$CH$_3$

HSCH$_2$CH$_2$CH$_3$

HSCH(CH$_3$)$_2$

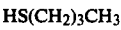
HS(CH$_2$)$_3$CH$_3$

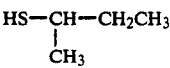
HS—CH—CH$_2$CH$_3$
     |
     CH$_3$

HSCH$_2$CH(CH$_3$)$_2$

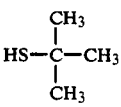
         CH$_3$
         |
HS—C—CH$_3$
         |
         CH$_3$

-continued

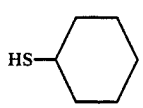

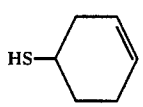

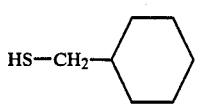

HS—CH$_2$—CH=CH$_2$

HS—CH$_2$—CH=C(CH$_3$)$_2$

HS—CH$_2$—C≡CH

HS—CH$_2$—C≡C—CH$_3$

HS(CH$_2$)$_n$OR$^1$ n = 2-4, R$^1$ = H, $\overset{O}{\overset{\|}{C}}$CH$_3$, CH$_3$ HS(CH$_2$)$_n$$\overset{O}{\overset{\|}{C}}$XR
n = 1-3, X = O, NH, NR$^1$; R, R$^1$ = H, CH$_3$ HS(CH$_2$)$_n$NH$_2$
n = 2-4

HS(CH$_2$)$_n$NHR$^1$ n = 2-4, R$^1$ = CH$_3$, CH$_2$CH$_3$, CH$_2$CH$_2$CH$_3$, $\overset{O}{\overset{\|}{C}}$CH$_3$ HS(CH$_2$)$_n$NR$^1$R$^2$
n = 2-4, R$^1$/R$^2$ = CH$_3$, CH$_2$CH$_3$

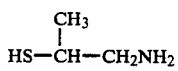

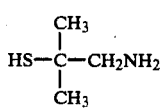

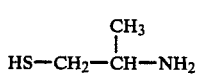

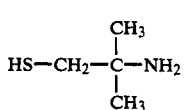

HS—CH$_2$CH$_2$SCH$_3$

HS—CH$_2$CH$_2$NHC(CH$_3$)$_3$

-continued

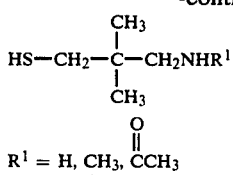
R$^1$ = H, CH$_3$, $\overset{O}{\overset{\|}{C}}$CH$_3$

HS—CH$_2$CH$_2$—NH—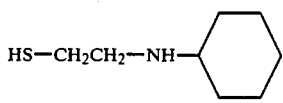

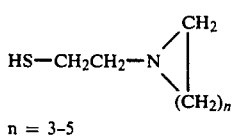
n = 3-5

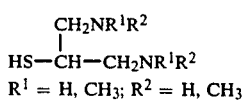
R$^1$ = H, CH$_3$; R$^2$ = H, CH$_3$

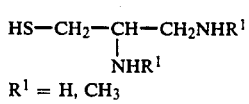
R$^1$ = H, CH$_3$

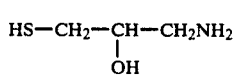

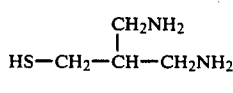

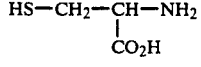

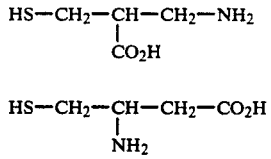

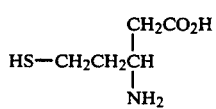

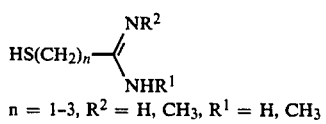

HS(CH$_2$)$_n$$\overset{NR^2}{\underset{NHR^1}{C}}$
n = 1-3, R$^2$ = H, CH$_3$, R$^1$ = H, CH$_3$ HS—CH=CH—NH$\overset{O}{\overset{\|}{C}}$CH$_3$

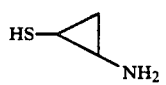

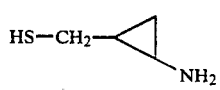

-continued
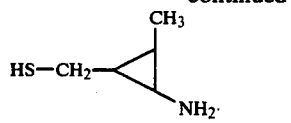
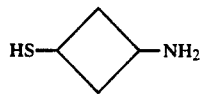
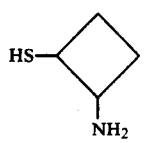
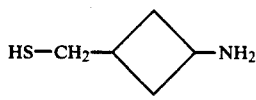
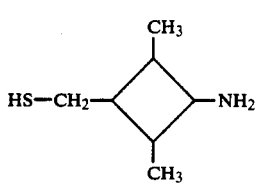
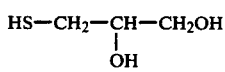
5-thio-D-glucose
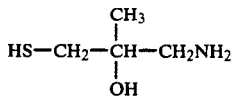
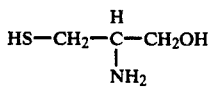
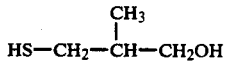
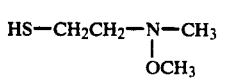
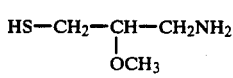
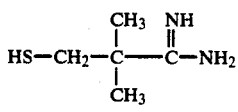
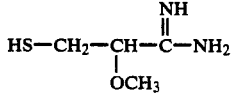
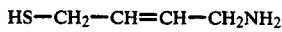
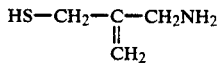
-continued
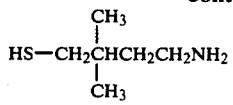
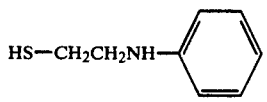
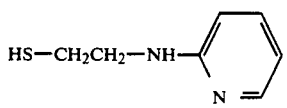
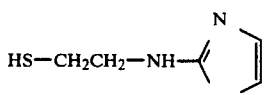
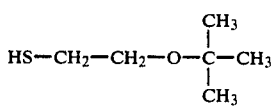
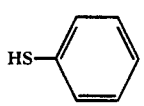
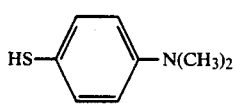
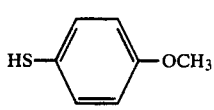
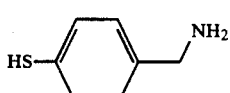
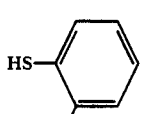
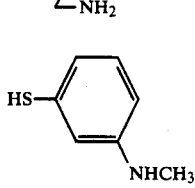
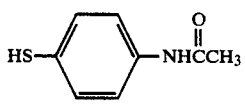
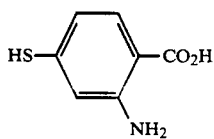

-continued
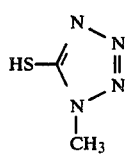
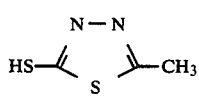
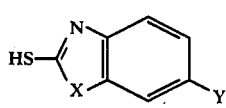
X = N, O   Y = H
X = S       Y = H, Cl, OCH₂CH₃
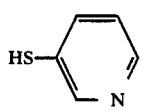
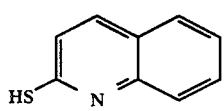
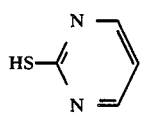
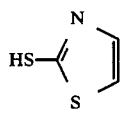
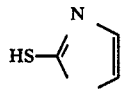
R = H, CH₃
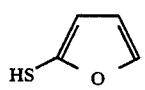
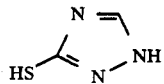
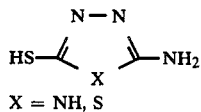
X = NH, S
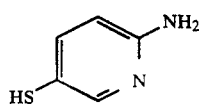
-continued
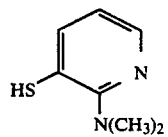
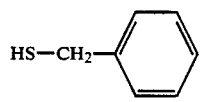
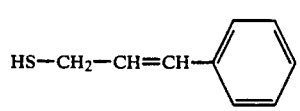
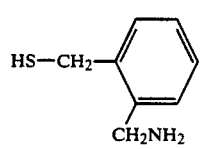
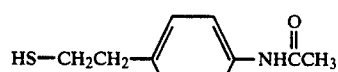
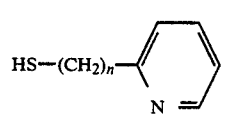
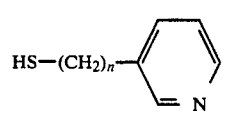
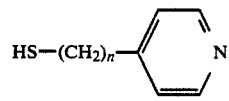
n = 1,2
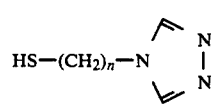
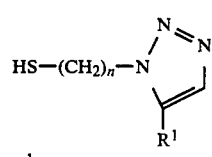
$R^1 = OCH_2CH_3$
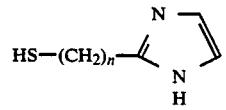
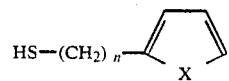

-continued
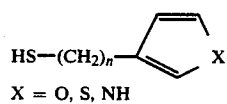
X = O, S, NH
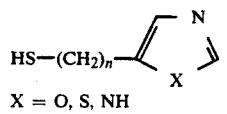
X = O, S, NH
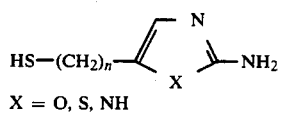
X = O, S, NH
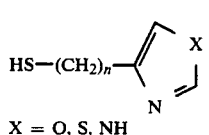
X = O, S, NH
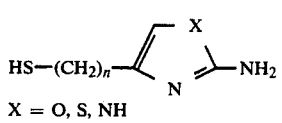
X = O, S, NH
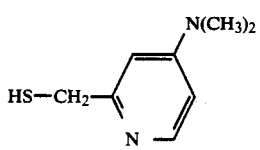
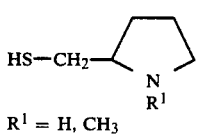
R¹ = H, CH₃
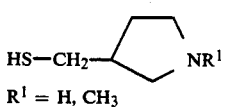
R¹ = H, CH₃
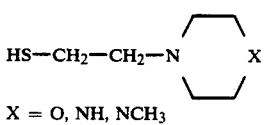
X = O, NH, NCH₃
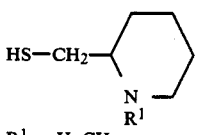
R¹ = H, CH₃
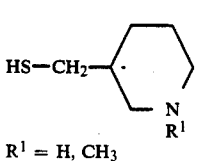
R¹ = H, CH₃
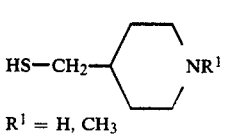
R¹ = H, CH₃
-continued
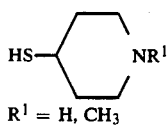
R¹ = H, CH₃
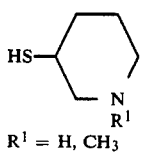
R¹ = H, CH₃
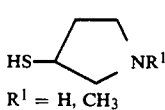
R¹ = H, CH₃
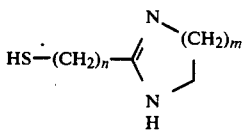
n = 1-3, m = 1-3
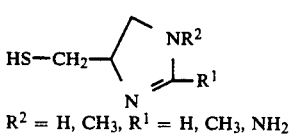
R² = H, CH₃, R¹ = H, CH₃, NH₂
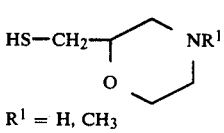
R¹ = H, CH₃
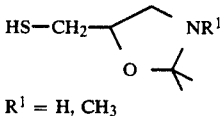
R¹ = H, CH₃
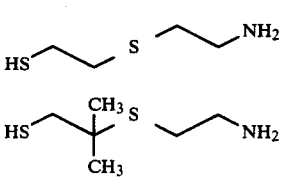
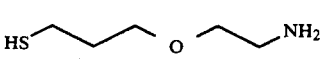
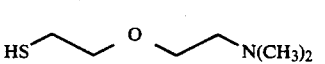
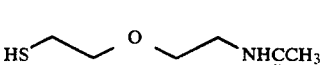
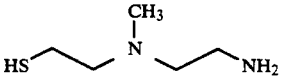
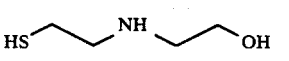
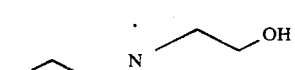

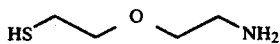

ACTIVITY AGAINST P-388 MURINE LEUKEMIA

Table I contains the results of laboratory tests with CDF$_1$ female mice implanted intraperitoneally with a tumor inoculum of 10$^6$ ascites cells of P-388 murine leukemia and treated with various doses of either a test compound of Formulas I or II, or with mitomycin C. The compounds were administered by intraperitoneal injection. Groups of six mice were used for each dosage amount and they were treated with a single dose of the compound on the day of inoculation. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. The "maximum effect" in the following Table is expressed as % T/C and the dose giving that effect is given. The values in parenthesis are the values obtained with mitomycin C as the positive control in the same experiment. Thus a measure of the relative activity of the present substances to mitomycin C can be estimated. A minimum effect in terms of % T/C was considered to be 125. The minimum effective dose reported in the following Table is that dose giving a % T/C of approximately 125. The two values given in each instance in the "average weight change" column are respectively the average weight change per mouse at the maximum effective dose and at the minimum effective dose.

TABLE I

| | Inhibition of P-388 Murine Leukemia | | | |
|---|---|---|---|---|
| | Maximum Effect | | Minimum effective | Average weight |
| Compound No. | % T/C | dose[1] | dose[1] | change[2] |
| 1 (BL-6787) | >333(294) | 3.2(3.2) | 0.2 | −1.2, −0.3 |
| 3 (BL-6796) | >375(250) | 6.4(3.2) | <0.2 | −2.5, −0.9 |
| 4 (BL-6832) | 172(194) | 6.4(3.2) | 0.8 | −2.8, −0.9 |
| 5 (BL-6790) | >333(294) | 12.8(3.2) | <0.2 | −2.4, 0 |
| 6 (BL-6789) | 183(294) | 12.8(3.2) | 0.4 | −0.6, +0.8 |
| 7 (BL-6788) | 200(294) | 12.8(3.2) | 0.2 | −0.6, −0.2 |
| 8 (BL-6795) | 188(250) | 6.4(3.2) | 0.8 | −0.8, +0.1 |
| 9 (BMY-25036) | 219(319) | 3.2(3.2) | <0.2 | −1.3, −0.6 |
| 11 (BMY-25066) | 194(194) | 3.2(1.6) | <0.2 | −1.8, −0.7 |
| 12 (BMY-25067) | 331(194) | 12.8(1.6) | <0.2 | −3.3, −1.1 |

[1]mg/kg of body weight
[2]grams per mouse, days 1-6, at maximum and minimum effective doses Table II contains results of antitumor tests using the B16 melanoma grown in mice. BDF$_1$ mice were employed and inoculated subcutaneously with the tumor implant. A 60 day protocol was used. Groups of ten mice were used for each dosage amount tested and the mean survival time for each group was determined. Control animals inoculated in the same way as the test animals and treated with the injection vehicle and no drug exhibited a mean survival time of 24.5 days. The survival time relative to that of the controls (% T/C) was used as a measure of effectiveness, and the maximal effective dose and minimal effective dose for each test compound was determined. The minimal effective dose was defined as that dose exhibiting a % T/C value of 125. For each dosage level, the test animals were treated with the test compound on days 1, 5, and 9 by the intravenous route.

TABLE II

| | Inhibition of B16 Melanoma | | | |
|---|---|---|---|---|
| Compound No. | Maximum Effect | | Minimum Effective Dose[1] | Average Wt. Change[2] |
| | % T/C | Dose[1] | | |
| 1 (BL-6787) | 122 | 3.0 | 3.0 | −2.7, −2.7 |
| 6 (BL-6789) | 163 | 3.0 | <3.0 | −1.8, −1.8 |
| 6 (BL-6789)[3] | 161 | 6.0 | <3.0 | −1.4, −1.3 |

[1]mg/kg of body weight
[2]grams per mouse, days 1-15, at maximum and minimum effective doses
[3]treatment on days 5, 9, and 13

Compound No. 3 (BL-6796) was also evaluated for its effectiveness against the B16 melanoma grown in BDF$_1$ mice. In this experiment the animals were inoculated with the tumor by the intraperitoneal route and treatment with the test compound was also by intraperitoneal injection. Treatment occurred on days 1, 5, and 9 as before and mean survival times were determined. Again the minimal effective dose was considered to be that dose yielding a % T/C 125. At a dose of 1 milligram per kilogram of Compound No. 3, 6 of 10 animals survived the entire 60 day test period (% T/C 235) and exhibited an average weight change of +0.1 grams on day 5. At a dose of 0.5 mg./kg. the mean survival time was 42.0 (% T/C 165) indicating that the minimal effective dose is less than 0.5 mg./kg. In the same test, mitomycin C exhibited % T/C 165 at a dose of 3 mg./kg. This was the maximal effective dose of mitomycin C in this experiment. It is thus evident that Compound No. 3 is several fold more potent against B16 melanoma in mice than mitomycin C.

The effects of Compounds 1 (BL-6787) and 3 (BL-6796) administered intravenously on the total and differential white blood cell (WBC) counts of mice were determined. Both compounds were found to be myelosuppressive, but apparently less so that mitomycin C. The results are given in Table III. The data for Compound 1 and mitomycin C were obtained in the same experiment, thus affording a direct comparison. Compound 1 was somewhat less myelosuppresive. The data for Compound 3, from a separate experiment, suggest still less myelosuppression, but a direct comparison with the other two compounds was not available.

TABLE III

| | White Blood Cell Counts | | | | |
|---|---|---|---|---|---|
| Compound No. | Dose (mg./kg., iv) | | Cells per cc. (×10$^3$) | | |
| | | | Pretreatment | Day 4 | Day 7 |
| 1 (BL-6787) | 6.4 | t* | 10 ± 0.7 | 4 ± 0.5 | 8 ± 0.8 |
| | | n | 1.5 ± 0.3 | 0.2 ± 0.04 | — |
| | | l | 8.2 ± 0.6 | 3.7 ± 0.5 | — |
| 1 (BL-6787) | 3.2 | t | 10 ± 0.6 | 7 ± 0.5 | 7 ± 0.7 |
| | | n | 1.0 ± 0.2 | 0.6 ± 0.1 | — |
| | | l | 9.1 ± 0.8 | 6.2 ± 0.5 | |
| 3 (BL-6796) | 8.8 | t | 10 ± 0.6 | 4 ± 0.7 | 11 ± 0.7 |
| | | n | 1.5 ± 0.1 | 0.5 ± 0.1 | — |
| | | l | 7.8 ± 0.6 | 3.7 ± 0.5 | — |

TABLE III-continued

White Blood Cell Counts

| Compound No. | Dose (mg./kg., iv) | | Cells per cc. ($\times 10^3$) | | |
|---|---|---|---|---|---|
| | | | Pretreatment | Day 4 | Day 7 |
| 3 (BL-6796) | 6.6 | t | 10 ± 0.4 | 5 ± 0.4 | 10 ± 0.9 |
| | | n | 1.7 ± 0.1 | 0.5 ± 0.1 | — |
| | | l | 8.3 ± 0.6 | 4.0 ± 0.3 | — |
| mitomycin C | 6.4 | t | 10.0 ± 0.2 | 3 ± 0.2 | 7 ± 0.5 |
| | | n | 1.0 ± 0.2 | 0.1 ± 0.02 | |
| | | l | 9.0 ± 0.3 | 2.5 ± 0.2 | |
| mitomycin C | 3.2 | t | 9.0 ± 0.7 | 4.0 ± 0.7 | 9 ± 0.5 |
| | | n | 0.7 ± 0.1 | 0.2 ± 0.02 | |
| | | l | 8.4 ± 0.6 | 4.0 ± 0.7 | |

*t = total white blood cell count
n = neutrophils
l = lympocytes

In view of the antitumor activity observed in experimental animal tumors, and the lack of undue myelosuppresive activity compared to mitomycin C, the invention includes use of the substances of the present invention for inhibiting mammalian tumors. For this purpose they are administered systematically to a mammal bearing a tumor in substantially non-toxic antitumor effective dose.

The compounds of the present invention are intended primarily for use by injection in much the same way and for some of the same purposes as mitomycin C. Somewhat larger or smaller doses may be employed depending upon the particular tumor sensitivity. They are readily distributed as dry pharmaceutical compositions containing diluents, buffers, stabilizers, solubilizers, and ingredients contributing to pharmaceutical elegance. These compositions are then constituted with an injectable liquid medium extemporaneously just prior to use. Suitable injectable liquids include water, isotonic saline, etc.

DESCRIPTION OF SPECIFIC EMBODIMENTS

All temperatures in the following experimental procedures are expressed in degrees Centigrade. Proton magnetic resonance spectra ($^1$H NMR) were recorded on a Varian XL 100 or on a Jeol FX-90Q (90 MHz) spectrometer in pyridine $d_5$ unless otherwise stated. Infra red (IR) spectra were obtained with a Bechman Model 4240 spectrophotometer and the IR figures are $\nu$max in cm$^{-1}$. Thin layer chromatography (TLC) was carried out on 0.25 mm E. Merck precoated silica gel plates (60F-254) using ultra violet light and/or iodine vapors as visualizing agent. Flash chromatography (*J. Org. Chem.* 14, 2923, 1978) was performed using Silica Woelm (32-63 um). Solvents were evaporated under reduced pressure and below 50° C.

PROCEDURE 1

7-[2-(Benzyldithio)ethylamino]-9a-methoxymitosane (Compound 1) Via Mitomycin A

To a solution of 200 mg. (0.28 mM) of S-benzyldithioethylamine, in 2 ml. of methanol containing 300 mg. of triethylamine there was added 99 mg. (28.3 mM) of mitomycin A in methanol (10 ml.) at 0°-4° C. The resulting solution was stirred at 20° C. for 2.5 hr. The progress of the reaction was monitored by TLC using a 10:90 v/v methanol-chloroform solvent system. The reaction mixture was concentrated under reduced pressure to a dry solid residue, which on flash chromatography (35 g silica gel) using 7:93 v/v methanol-dichloromethane (800 ml.) as eluant afforded the title compound (87 mg., 59%) as a pure amorphous solid.

$^1$H NMR (90 MHz, pyridine $d_5$, δ): 2.08(s, 3H), 2.74(m, 3H), 3.16(d, 1H, J=6 Hz), 3.24(s, 3H), 3.40-4.20(m, 6H), 4.04 (s, 2H), 4.56(d, 1H, J=14 Hz), 5.08(t, 1H, J=12 Hz), 5.40 (dd, 1H, J=6, 12 Hz), 7.44(bs, 5H).

IR(BKr), $\nu$max, cm$^{-1}$: 3440, 3350, 3290, 3060, 3020, 1720, 1635, 1560, 1325, 1060.

Anal. Calc'd for $C_{24}H_{28}N_4O_5S_2$: C, 55.80; H, 5.46; N, 10.84; S, 12.41. Found: C, 55.08; H, 5.31; N, 10.52; S, 12.10.

PROCEDURE 2

N-[2-(2-Aminoethyldithio)ethyl]acetamide (Compound 2)

a. Bunte Salt Method

A solution of 695 mg. of 2-aminoethanthiosulfuric acid (4.59 mM) in 7 ml. of methanol containing 318 mg. (7.95 mM) of sodium hydroxide was stirred for 10 minutes at room temperature and then cooled to 0°. N-Acetylcysteamine, 357 mg. (3.43 mM), was added to this solution and the solution was stirred for an additional 10 minutes. The resulting cloudy solution was diluted to about 60 ml. with methanol and this solution was then acidified by the careful additon of acetyl chloride (624 mg., 7.95 mM). The clear solution was evaporated to a waxy solid, which was directly used for conversion to Compound 3.

b. Sulfenylthiocarbonate Method

The method of S. J. Brois et al. (loc. cit.) was employed. Methyl-2-aminoethylsulfenylthiocarbonate hydrochloride in methanol solution was treated with acetylcysteamine at 0° C. The reaction, without triethylamine accelerator, was practically instantaneous.

PROCEDURE 3

7-[2-(2-Acetylaminoethyldithio)ethyamino]-9a-methoxymitosane (Compound 3)

To a solution of 100 mg. (0.29 mM) of mitomycin A in 4 ml. of methanol containing 200 mg. (198 mM) of triethylamine there was added at about 0° a solution of about 400 mg. of 2 in 2 ml. methanol. The precipitate which appeared was removed by filtration, and the clear filtrate was allowed to stand at room temperature for 4 hrs. The solution was evaporated to a dry residue and flash chromotagraphed on silica gel (10 g) using the gradient elution technique (4% to 8% methanol in methylene chloride). The desired product was the faster moving blue zone component which was isolated as an amorphous solid weighing 45 mg. (31.5%). An analytical sample was obtained by triturating the solid with 5% methylene chloride in hexane and drying the solid.

$^1$H NMR (100 MHz, pyridine $d_5$, δ): 2.06(s, 3H), 2.10(s, 3H), 2.76(bs, 1H), 2.80-3.20(m, 5H), 3.24(s, 3H), 3.60(dd, 1H, J=12 and 2 Hz), 3.70-4.10(m, 5H), 4.54(d, 1H, J=12 Hz), 5.04(t, 1H, J=10 Hz), 5.38(dd, 1H, J=4 and 10 Hz).

IR(KBr), $\nu$max, cm$^{-1}$: 3420, 3350, 3290, 1720, 1635, 1656, 1330, 1060.

Anal. Calc'd for $C_{21}H_{29}N_5O_6S_2$: C, 49.26; H, 5.67; N, 13.68; S, 12.51. Found: C, 49.33; H, 6.04; N, 13.20; S, 11.48.

PROCEDURE 4

7-[2-(Octyldithio)ethylamino]-9a-methoxymitosane (Compound 4) Via 7-Substituted Amidino-9a-methoxymitosane To a solution of 60 mg. (0.15 mM) 7-(dimethylaminomethylene)amino-9a-methoxymitosane in methanol (1 ml.) containing triethylamine (0.2 ml.) was added 139 mg. (0.54 mM) of 2-(octyldithio)ethylamine hydrochloride. The solution was allowed to stand at 0°–4° C. for 48 hrs. Thin layer chromatography using 10:90 v/v methanol-methylene chloride then revealed that the green-colored starting compound had been consumed, and a major blue zone (RF=0.6) was visible. The solution was concentrated under reduced pressure to a solid residue, which was flash chromatographed on silica gel (12 g) using 20:1 v/v methylene chloride-methanol as the eluting solvent. The title compound was obtained as an amorphous solid (27 mg., 34%) whose $^1$H NMR spectrum (100 MHz) is given in Table IV.

PROCEDURES 5–22

Application of Various Dithio Amines

The amines identified in Table IV may be caused to react as described in either of Procedures 1, 3, or 4 to produce the products of Formulas I and II which are identified in the table.

Analytical and spectral data for some of the foregoing substances and some identified in Table IV are presented in Table V.

TABLE IV

| | | | Additional Products of Formulas I and II | | |
|---|---|---|---|---|---|
| Proc. No. | Formula* | $R^7Alk_1$— or $R^8$— | $R^7Alk$, - or $R^8$ | $Alk_2$ | Amine Reactant |
| 5 | I | $H_2N(CH_2)_2$— | | —$(CH_2)_2$— | 2-aminoethyl disulfide |
| 6 | II | phenyl | | —$(CH_2)_2$— | 2-aminoethyl phenyl disulfide |
| 7 | II | n-butyl | | —$(CH_2)_2$— | 2-aminoethyl n-butyl disulfide |
| 8 | I | | | —$(CH_2)_2$— | N—[2-(2-aminoethyldithio)ethyl]-acetamide |
| (R is —COCH$_3$) | | $CH_3CONHCH_2CH_2$— | | | |
| 9 | I | $HOCH_2CH_2$— | | —$(CH_2)_2$— | 2-(2-aminoethyldithio)ethanol |
| 10 | II | 2-pyridyl | | —$(CH_2)_2$— | 2-(2-aminoethyldithio)pyridine |
| 11 | II | 4-methoxyphenyl | | —$(CH_2)_2$— | 2-aminoethyl 4-methoxyphenyl dissulfide |
| 12 | II | 4-nitrophenyl | | —$(CH_2)_2$— | 2-aminoethyl 4-nitrophenyl dissulfide |
| 13 | I | $C_6H_5CONH(CH_2)_2$— | | —$(CH_2)_2$— | N—[2-(2-aminoethyldithio)ethyl]-benzamide |
| 14 | I | 4-$CH_3O$-$C_6H_4$-$CONH(CH_2)_2$— | | —$(CH_2)_2$— | N—[2-(2-aminoethyldithio)ethyl]-anisamide |
| 15 | I | 4-$NO_2$-$C_6H_4$-$CONH(CH_2)_2$— | | —$(CH_2)_2$— | N—[2-(2-aminoethyldithio)ethyl]-4-nitrobenzamide |
| 16 | II | 4-chloro-2-naphthyl | | —$(CH_2)_2$— | 2-aminoethyl 4-chloro-2-naphthyl disulfide |
| 17 | II | $CH_3O_2CCHCH_2$—<br>\|<br>$NH_2OCHCH_2C_6H_5$ | | —$(CH_2)_2$— | S—(2-aminoethylthio)cysteine, methyl ester |
| 18 | II | $CH_3O_2CCHCH_2$—<br>\|<br>$NHCOCHCH_2C_6H_5$<br>\|<br>$NH_2$ | | —$(CH_2)_2$— | S—(2-aminoethylthio)phenyl-alanylcysteine, methyl ester |
| 19 | I | $CH_3O_2C(CH_2)_6$— | | —$(CH_2)_2$— | 6-mercaptoheptanoic acid, methyl ester |

TABLE IV-continued

Additional Products of Formulas I and II

| Proc. No. | Formula* | R⁷Alk₁— or R⁸— | R⁷Alk, - or R⁸ | Alk₂ | Amine Reactant |
|---|---|---|---|---|---|
| 20 | I | cyclopropyl-CH₂— | —(CH₂)₆— | | 6-[(cyclopropyl)methyldithio]-hexylamine |
| 21 | I | phenyl-OCH₂CH₂— | —(CH₂)₂— | | 2-aminoethyl 2-phenoxyethyl disulfide |
| 22 | II | pyrimidyl | | —(CH₂)₂— | 2-(2-aminoethyldithio)pyrimidine |
| 23 | II | 2-oxopyrrolidin-1-yl-(CH₂)₂— | | —(CH₂)₂— | 1-[2-(2-aminoethyldithio)ethyl]-2-pyrrolidone |
| 24 | II | benzimidazol-2-yl | | —(CH₂)₂— | 2-[2-(aminoethyldithio)]-benzimidazole |
| 25 | I | $C_2H_5OC(O)$—NHCH₂CH₂ | | —(CH₂)₂— | 2-aminoethyl 2-ethoxycarbonyl-aminoethyl disulfide |
| 26 | I | $H_2NC(=NH)$—NH(CH₂)₃— | | —(CH₂)₂— | 2-aminoethyl 3-guanidinopropyl disulfide |
| 27 | I | Cl(CH₂)₂N(NO)CONH(CH₂)₂— | | —(CH₂)₂— | H₂NCH₂CH₂—SS—CH₂ ClCH₂CH₂N(NO)CONHCH₂ |
| 28 | II | | 2-nitrophenyl | —(CH₂)₂— | 2-aminoethyl 2-nitrophenyl disulfide** |
| 29 | II | | 2,4-dinitrophenyl | —(CH₂)₂— | 2-aminoethyl 2,4-dinitrophenyl disulfide** |
| 30 | II | | 3-nitro-2-pyridyl | —(CH₂)₂— | 2-aminoethyl 3-nitro-2-pyridyl disulfide |
| 31 | II | | 5-nitro-2-pyridyl | —(CH₂)₂— | 2-aminoethyl 5-nitro-2-pyridyl disulfide |

*R of Formulas I and II is H unless indicated otherwise
**Prepared by reaction of 2-nitrophenylsulfenyl chloride or 2,4-dinitrophenylsulfenyl chloride with cysteamine hydrochloride in tetrahydrofuran at 0° C. according to the general method of Y. Nagao et al., Tetrahedron Letters No. 50, pp 5021–5024 (1978).

TABLE V

| Compound | ¹H NMR Data (pyridine d₅, δ) | IR(KBr), ν max cm⁻¹ | Elemental Analysis |
|---|---|---|---|
| 4ª | 0.87(m, 3H), 1.23(bs, 10H), 1.70 (m, 2H), 2.17(s, 3H), 2.76(t, 2H, 7 Hz), 2.76(bs, 1H), 3.00 (t, 2H, 7 Hz), 3.14(d, 1H, 4 Hz), | 3440, 3350, 3290, 2950, 2920, 1720, 1635, 1560, 1320, 1060 | T. C, 55.74; H, 7.11; N, 10.40; S, 11.90 F. C. 56.09; H, 6.86; N, 10.48; S, 12.15 |

TABLE V-continued

| Compound | ¹H NMR Data (pyridine $d_5$, δ) | IR(KBr), $\nu$max cm$^{-1}$ | Elemental Analysis |
|---|---|---|---|
| | 3.24(s, 3H), 3.60(dd, 1H, 3, 12 Hz), 3.80–4.20(m, 3H), 4.54(d, 1H, 12 Hz), 5.06(t, 1H, 10 Hz), 5.40(dd, 1H, 4, 10 Hz) | | |
| 5[a] | 2.08(s, 3H), 2.72(d, 1H, 4 Hz), 2.80–3.30(m, 5H), 3.20(s, 3H), 3.44(t, 2H), 3.56(dd, 1H, 2, 12 Hz), 3.70–4.10(m, 3H), 4.48 (d, 1H, 12 Hz), 4.96(t, 1H, 10 Hz), 5.33(dd, 1H, 10, 4 Hz) | 3400, 3280, 2930, 1710, 1635, 1560, 1330, 1060 | T. C, 45.13; H, 6.17; N, 13.85; S, 12.68 F. C, 44.82; H, 5.33; N, 12.96; S, 12.44 |
| 6[b] | 2.04(s, 3H), 2.76(bs, 1H), 3.00 (m, 3H), 3.26(s, 3H), 3.62(d, 1H, 14 Hz), 3.72–4.12(m, 3H), 4.52(d, 1H, 14 Hz), 5.40(dd, 1H, 6, 12 Hz) | 3440, 3350, 3290, 2960, 2930, 1720, 1635, 1560, 1330, 1060 | T. C, 53.06; H, 5.42; N, 10.76; S, 12.32 F. C, 53.41; H, 4.73; N, 10.70; S, 12.52 |
| 7[b] | 0.60–1.80(m, 7H), 2.12(s, 3H), 2.72(m, 3H, 2.96(t, 2H, 8 Hz), 3.12(d, 1H), 3.24(s, 3H), 3.60(dd, 1H, 2, 14 Hz), 3.82(m, 3H), 4.50(d, 1H, 14 Hz), 5.36(dd, 1H, 6, 12 Hz) | 3440, 3350, 3290, 2950, 2920, 1715, 1635, 1560, 1320, 1060 | T. C, 52.26; H, 6.26; N, 11.61; S, 13.29 F. C, 52.78; H, 6.87; N, 9.89; S, 10.38 |
| 8[a,c] | 2.05(s, 3H), 2.13(s, 3H), 2.15 (s, 3H), 3.00(m, 4H), 3.20(s, 3H), 3.48(dd, 1H), 3.60(dd, 1H, 2, 14 Hz), 3.77(d, 1H, 5 Hz), 3.90(m, 4H), 4.06(dd, 1H, 4, 10 Hz), 4.59(t, 1H, 10 Hz), 4.74 (d, 1H, 14 Hz), 5.61(dd, 1H, 4, 10 Hz), 7.28, 7.64 | 3420, 3350, 3290, 2830, 1710, 1650, 1635, 1560, 1320, 1060 | T. C, 49.90; H, 5.64; N, 12.65; S, 11.58 F. C, 48.95; H, 5.37; N, 12.22; S, 12.54 |
| 9[b] | 2.12(s, 3H), 2.76(bs, 1H), 3.12 (m, 5H), 3.24(s, 3H), 3.60 (dd, 1H, 2, 14 Hz), 4.00(m, 6H), 4.52 (d, 1H, 14 Hz), 5.04(t, 1H, 12 Hz), 5.40(dd, 1H, 6, 12 Hz) | 3430, 3360, 3280, 2920, 1710, 1630, 1550, 1325, 1055 | T. C, 48.50; H, 5.57; N, 11.91; S, 13.63 F. C, 48.73; H, 5.82; N, 11.06; S, 13.67 |
| 10[b] | 2.04(s, 3H), 2.74(bs, 1H), 3.08 (m, 3H), 3.24(s, 3H), 3.60(dd, 1H, 2, 14 Hz), 3.92(m, 3H), 4.52(d, 1H, 14 Hz), 5.02(t, 1H, 12 Hz), 5.36(dd, 1H, 6, 12 Hz), 7.16, 7.56, 8.72 | 3430, 3350, 3280, 2930, 1720, 1630, 1555, 1325, 1060, | T. C, 52.47; H, 5.00; N, 13.91; S, 12.73 F. C, 46.37; H, 4.42; N, 11.88; S, 11.26 |
| 11[b] | 2.04(s, 3H), 2.72(bs, 1H), 3.04 (m, 3H), 3.22(s, 3H), 3.58(dd, 1H, 2, 14 Hz), 3.68(s, 3H), 3.92(m, 3H), 4.52(d, 1H, 14 Hz), 5.04(t, 1H, 12 Hz), 5.38(dd, 1H, 6, 12 Hz), 7.34 (AB quartet, 4H) | 3440, 3360, 3300, 2940, 1720, 1635, 1555, 1335, 1060 | T. C, 54.12; H, 5.30; N, 10.52; S, 12.04 F. C, 53.30; H, 5.32; N, 10.61; S, 12.13 |
| 12[b] | 2.04(s, 3H), 2.74(bs, 1H), 3.08 (m, 3H), 3.24(s, 3H), 3.60(dd, 1H, 2, 14 Hz), 3.96(m, 3H), 4.52(d, 1H, 14 Hz), 5.04(t, 1H, 12 Hz), 5.40 (dd, 1H, 6, 12 Hz), 8.04 (AB quartet, 4H) | 3460, 3360, 3300, 2940, 1720, 1635, 1555, 1340, 1060 | T. C, 50.45; H, 4.60; N, 12.79; S, 11.71 F. C, 49.25; H, 4.55; N, 12.78; S, 11.69 |
| 28[e] | 2.00(s, 3H), 2.17(m, 1H), 2.77(bs, 1H) 3.03(t, 2H), 3.17(bs, 1H), 3.23(s, 3H), 3.60(d, 1H, 12.8 Hz), 3.87(dt, 2H), 4.00(dd, 1H, 4.2 Hz, 11.1 Hz), 4.51(d, 1H, 12.8 Hz), 5.10(t, 1H), 5.40(dd, 1H, 4.2 Hz, 10.3 Hz), 7.32(m, 2H), 7.71(t, 1H), 8.28 (dd, 1H) | 3460, 3350, 3285, 2940, 1720, 1635, 1560, 1510, 1450, 1335, 1060 | T: C, 48.33; H, 4.47; N, 12.04 F: C, 48.37; H, 4.56; N, 12.02 (corrected for 0.4 M % CH$_2$Cl$_2$) |
| 29[e] | 2.03(s, 3H), 2.15(bs, 1H), 2.75(bs, 1H), 3.14(t, 2H), 3.24(s, 3H), 3.24(bs, 1H), 3.60(d, 1H), 3.94(dt, 2H), 4.00(dd, 1H, 4.1 Hz, 11.2 Hz), 4.50(d, 1H, 12.7 Hz), 5.36(dd, 1H, 4.1 Hz, 10.3 Hz), 7.32(m, 1H), 8.53(m, 1H) | 3460, 3360, 3290, 3105, 2940, 1715, 1635, 1555, 1340, 1060 | T: C, 44.51; H, 3.97; N, 13.25 F: C, 44.56; H, 3.93; N, 12.85 (corrected for 0.5 M % CH$_2$Cl$_2$) |
| 30[b] | 2.08(s, 3H), 2.18(m, 1H), 2.77(bs, 1H), 3.17 (m, 3H), 3.24(s, 3H), 3.61(d, 1H, 12.4 Hz), 3.87(dt, 2H), 4.03(dd, 1H, 4.1 Hz, 11.1 Hz), 4.55(d, 1H, 12.7 Hz), 5.12(t, 1H), 5.42(dd, 1H, 4.2 Hz, 10.3 Hz), 7.33(dd, 1H, 4.8 Hz, 8.4 Hz), 7.85(t, 1H), 8.50(d, 1H, 8.2 Hz), 9.13(d, 1H, 4.8 Hz) | 3460, 3350, 3280, 3065, 2930, 1720, 1630, 1550, 1335, 1060 | T: C, 45.72; H, 4.26; N, 14.22 F: C, 45.72; H, 4.39; N, 14.31 (corrected for 0.5 M % CH$_2$Cl$_2$) |
| 31[b] | 2.04(s, 3H), 2.04(bs, 1H), 2.76(bs, 1H), 3.12(m, 3H), 3.22(s, 3H), 3.56(d, 1H, 14 Hz), 3.90(m, 3H), 4.48(d, 1H, 14 Hz), 5.00(t, 1H, 12.0 Hz), 5.36(dd, 1H, 4.3 Hz, 12.0 Hz), 7.92(d, 1H, 10.0 Hz), 8.52 | 3465, 3345, 3280, 3060, 2930, 1720, 1630, 1585, 1555, 1340, 1055 | T: C, 46.18; H, 4.29; N, 14 F: C, 46.19; H, 4.32; N, 13.95 (corrected for 0.4 % CH$_2$Cl$_2$) |

TABLE V-continued

| Compound | $^1$H NMR Data (pyridine $\underline{d}_5$, δ) | IR(KBr), $\nu$max cm$^{-1}$ | Elemental Analysis |
|---|---|---|---|
| | (dd, 1H, 4 Hz, 10 Hz), 9.52(d, 1H, 4 Hz) | | |

[a]100 MHz NMR Spectrum
[b]90 MHz NMR Spectrum
[c]Prepared by acylation of Compound 5 with acetic anhydride and pyridine
[d]T = Theory, F = Found
[e]360 MHz NMR Spectrum

TABLE I

Addendum
Inhibition of P-388 Murine Leukemia[3]

| Compound No. | Maximum % T/C | Effect. Dose[1] | Minimum Effective Dose[1] | Average Weight Change[2] |
|---|---|---|---|---|
| 28 (BMY-25828) | 220(270) | 6.4(4.8) | <0.4 | −1.1, +3.2 |
| 29 (BMY-25829) | 170(270) | 3.2(4.8) | <0.2 | +2.6, +2.7 |

TABLE I-continued

Addendum
Inhibition of P-388 Murine Leukemia[3]

| Compound No. | Maximum % T/C | Effect. Dose[1] | Minimum Effective Dose[1] | Average Weight Change[2] |
|---|---|---|---|---|
| 30 (BMY-25827) | 200(270) | 12.8(4.8) | <0.4 | −3.2, +1.0 |
| 31 (BMY-25830) | 170(270) | 3.2(4.8) | <0.2 | +1.3, +0.5 |

[1]mg/kg body weight
[2]grams per mouse, days 1-7, at maximum and minimum effective dose
[3]male CDF$_1$ mice

What is claimed is:
1. The compound having the chemical name 7-[2-(4-nitrophenyldithio)ethylamino]-9a-methoxymitosane.

* * * * *